United States Patent
Dirauf et al.

(10) Patent No.: US 9,192,785 B2
(45) Date of Patent: Nov. 24, 2015

(54) DEVICE AND METHOD TO DETERMINE THE POSITION OF A COMPONENT THAT IS MOVEABLE IN A LINEAR MANNER ALONG AN ASSIGNED AXIS

(71) Applicants: Franz Dirauf, Ebensfeld (DE); Kerstin Farmbauer, Pressath (DE); Carsten Schuh, Baldham (DE); Thorsten Steinkopff, Egmating (DE); Andreas Wolff, Munich (DE)

(72) Inventors: Franz Dirauf, Ebensfeld (DE); Kerstin Farmbauer, Pressath (DE); Carsten Schuh, Baldham (DE); Thorsten Steinkopff, Egmating (DE); Andreas Wolff, Munich (DE)

(73) Assignee: Siemens Aktiengesellschaft, München (DE)

( * ) Notice: Subject to any disclaimer, the term of this patent is extended or adjusted under 35 U.S.C. 154(b) by 565 days.

(21) Appl. No.: 13/623,900

(22) Filed: Sep. 21, 2012

(65) Prior Publication Data

US 2013/0077444 A1    Mar. 28, 2013

(30) Foreign Application Priority Data

Sep. 22, 2011 (DE) .......... 10 2011 083 206
Jul. 6, 2012 (DE) .......... 10 2012 211 816

(51) Int. Cl.
| | |
|---|---|
| G01S 3/80 | (2006.01) |
| H04R 17/00 | (2006.01) |
| A61N 5/10 | (2006.01) |
| A61B 6/00 | (2006.01) |
| G21K 1/04 | (2006.01) |

(52) U.S. Cl.
CPC .......... A61N 5/1045 (2013.01); A61N 5/1048 (2013.01); *A61B 6/4035* (2013.01); *G21K 1/046* (2013.01)

(58) Field of Classification Search
CPC . A61N 5/1048; A61N 5/1045; A61B 6/4035; G21K 1/046
USPC .......................................... 367/118
See application file for complete search history.

(56) References Cited

U.S. PATENT DOCUMENTS

| | | | |
|---|---|---|---|
| 7,792,252 B2 | 9/2010 | Bohn | |
| 2005/0185766 A1 | 8/2005 | Tsujita | |
| 2010/0281983 A1* | 11/2010 | Dirauf et al. | 73/627 |
| 2013/0077444 A1* | 3/2013 | Dirauf et al. | 367/118 |

FOREIGN PATENT DOCUMENTS

| | | |
|---|---|---|
| DE | 10 2008 003 879 A1 | 7/2008 |
| DE | 10 2008 004 867 A1 | 8/2008 |
| DE | 10 2009 020 676 A1 | 11/2010 |

OTHER PUBLICATIONS

German Office Action dated May 5, 2012 for corresponding German Patent Application No. DE 10 2011 083 206.8 with English translation.

* cited by examiner

*Primary Examiner* — Daniel Pihulic
(74) *Attorney, Agent, or Firm* — Lempia Summerfield Katz LLC

(57) ABSTRACT

A device and a method to determine a position of a component that is moveable in a linear manner along an assigned axis are provided. A reference element that extends in a direction of the assigned axis is assigned to the component. The component may be brought into mechanical contact with the reference element. A respective piezo transducer is arranged on the reference element to generate and receive vibrations in a material used for the reference element.

18 Claims, 1 Drawing Sheet

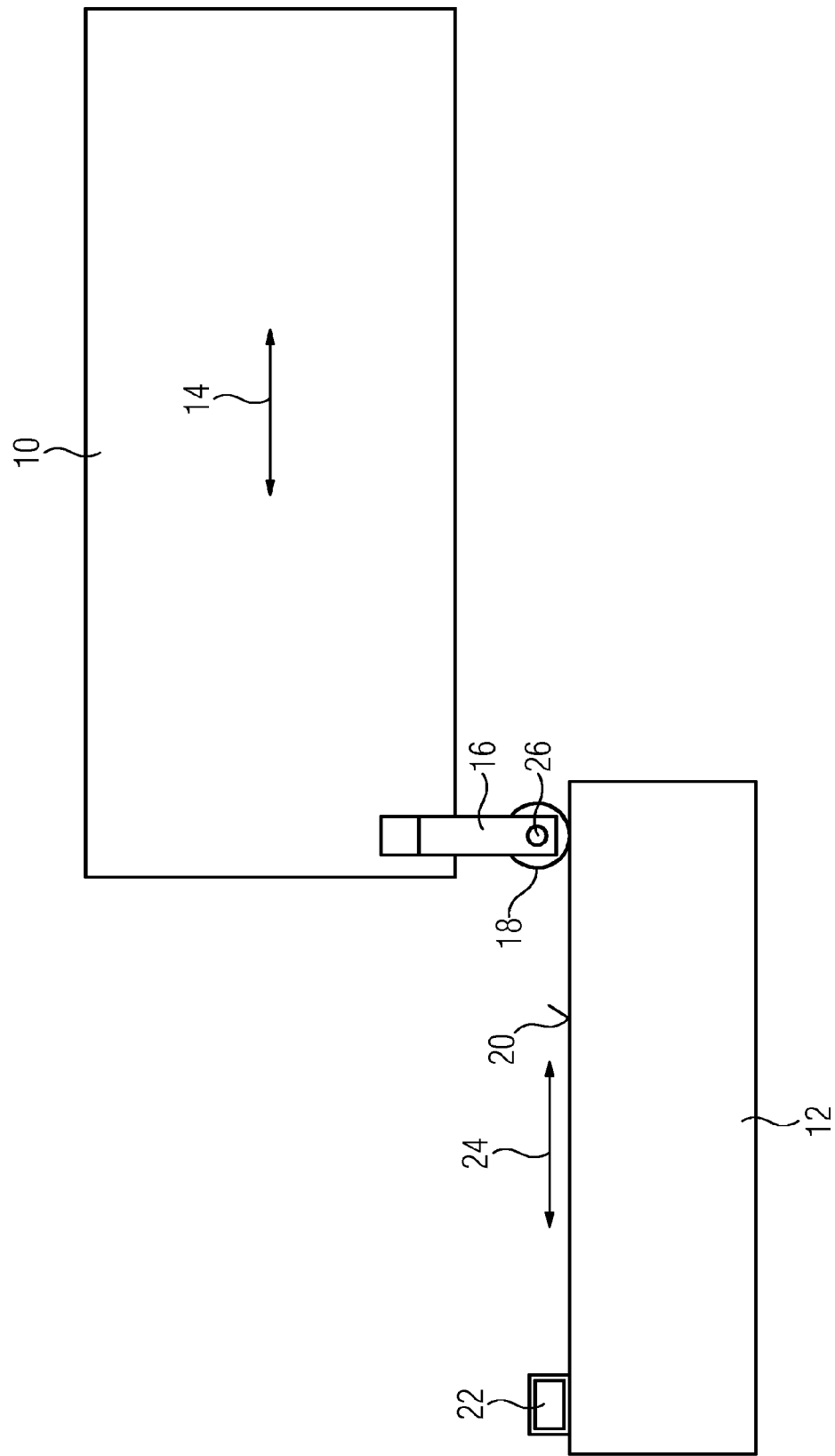

DEVICE AND METHOD TO DETERMINE THE POSITION OF A COMPONENT THAT IS MOVEABLE IN A LINEAR MANNER ALONG AN ASSIGNED AXIS

This application claims the benefit of DE 10 2011 083 206.8, filed on Sep. 22, 2011. This application also claims the benefit of DE 10 2012 211 816.0, filed on Jul. 6, 2012.

BACKGROUND

The present embodiments relate to a device and a method to determine the position of a component that is moveable in a linear manner along an assigned axis according.

In many technical applications, the position of moveable components is to be determined precisely. This may be achieved by integration over the movement trajectory of assigned drives (e.g., stepper motors or linear drives). For many applications such as, for example, in medical technology, measurement technology, optics or the like, the accuracy of such measurement methods is not sufficient.

An example of the need for precise position determinations in medical technology may be found in the field of multi-leaf collimators.

Multi-leaf collimators are used to shape the beam of an X-ray beam that may be generated by a linear accelerator in therapeutic radiation therapy. Such a collimator encompasses a plurality of leaves of a radio-opaque material (e.g., tungsten). The leaves are arranged in a moveable manner such that, by the positioning the leaves, the cross-sectional profile of the beam may be adjusted to match contours of the perimeter of an area of tissue located in the X-ray beam that is to be treated. This provides that the tissue to be treated (e.g., a tumor) receives the desired dose of radiation, while the surrounding tissue is exposed to as little radiation as possible.

In modern methods of radiation therapy such as, for example, in dynamic arc irradiation, the position of the leaves is to be constantly adjusted since the beam moves in relation to the patient, and the contour of the perimeter of the tissue that is to be irradiated therefore changes as a function of an angular position of the beam to the patient. In intensity-modulated treatment, the aim of which is to distribute the radiation as regularly as possible in the zone to be irradiated and thus to make up for imbalances in the passage of radiation through the body, a constant adjustment of the position of the collimator leaves is provided.

In order to provide a reliable operation of such a multi-leaf collimator, each position of the leaves is to be known precisely at all times. From the prior art, this may be achieved by installing a piezo transducer in direct contact with an edge of a respective leaf and generating surface waves in the leaf by using the piezo transducer. Such surface waves (e.g., edge waves) then run along the edge of the leaf and are reflected on a defined obstacle (e.g., on a corner of the leaf). The relative position of the leaf may be determined from a signal propagation time for the signal that has been transmitted or reflected.

SUMMARY AND DESCRIPTION

The disadvantage of the design of the prior art is that abrasion occurs between the moveable leaf and the piezo transducer. This may be reduced by providing targeted coatings on the piezo transducer using, for example, sputter coatings or adhesive wafers of hard material. However, there is still significant abrasion, restricting the life of the system and requiring costly inspections and maintenance.

Comparable problems also occur when determining the position of other medical technology devices (e.g., in examination couches that are intended for use in investigations involving image-generating methods).

The present embodiments may obviate one or more of the drawbacks or limitations in the related art. For example, a device and a method for determining a position of a component that is moveable in a linear manner along an assigned axis that allow a low-abrasion operation while providing reliable position determination are provided.

To determine the position of a component that is moveable in a linear manner along at least one axis, a reference element extending in the direction of the axis is assigned to the component. The component may be brought into mechanical contact with the reference element. A piezo transducer is arranged on the reference element to generate and receive vibrations in the material used for the reference element.

In contrast with the prior art, there is therefore no direct contact between the piezo transducer and the moveable component. For example, the piezo transducer is securely mounted and therefore does not have a contact surface that is in moveable contact with a further component. This completely avoids abrasion on the piezo transducer, such that there is no need for costly inspections and maintenance.

In the device, the position of the component is determined by the generation of surface waves that are generated not in the leaf itself, but in the reference element. The surface waves emanating from the piezo transducer run along the reference element and are reflected at a point of contact between the reference element and the moveable component. The position of the component may be determined from the signal propagation time between the transmission of the signal and the signal being received and reflected. This allows a reliable position determination.

The reference element may be configured as a panel arranged on a supporting frame. The panel-shaped design allows a good propagation of surface waves.

In this design, it is useful if the moveable component is in mechanical contact with one edge of the reference element, on which the respective piezo transducer is arranged. Along the edge of such a panel-shaped reference element, a good wave propagation is possible. For example, along the edge, the waves are propagated as transverse waves while the waves run through the body of the reference element mainly in the form of longitudinal waves. The transverse waves may be reflected in a reliable manner and are therefore detected with a good signal-noise ratio.

The mechanical contact between the moveable component and the reference element may be achieved using a sliding or rolling element. A mechanical contact of this kind allows a low-abrasion operation, such that long life is provided, and costly maintenance may essentially be avoided.

In order to allow a reliable reflection of the signals generated by the piezo transducer, there may be a contact pressure of 5 to 10 N between the sliding or rolling element and the reference element.

Advantageously, the reference element and the sliding or rolling element are magnetized. An option, for example, is the use of ferromagnetic (e.g., permanently magnetic) materials for the reference element and the sliding or rolling element. Through magnetization, the required contact pressure between the two elements may be generated without additional mechanical and hence abrasion-susceptible elements such as springs, for example, becoming necessary.

A greater magnetic contact pressure between the sliding or rolling element and the reference element may be achieved if the sliding or rolling element is moveable in a groove of the reference element. In order to reduce the lateral contact between the sliding or rolling element and the groove and thus to avoid abrasion due to unnecessary friction, the groove may be conically shaped. As an alternative or addition thereto, side walls of the groove or side surfaces of the sliding or rolling element may be coated with a non-magnetic material such that, between the two elements, there are no magnetic forces that do not contribute to the desired contact pressure. This reduces the friction between the elements and thus reduces abrasion.

In one embodiment, the device is configured to determine the position of a leaf in a leaf collimator for shaping a beam in an X-ray device. As a result of the small space the device uses, this may be suitable in order to allow precision in the adjustment of the leaves.

In another embodiment, the device is configured to determine the position of an examination couch of a medical device. By using the device, the precision in the position adjustment (e.g., in examination couches in devices for image-generating methods) may be guaranteed.

In one embodiment, a method for determining a position of a component that is moveable in a linear manner along at least one axis is provided. A piezo transducer that is attached to a reference element extending in the direction of the axis is used to generate a vibration signal in the reference element. This vibration signal (e.g., in the form of a surface wave or an edge wave) is reflected on a point of contact between the moveable component and the reference element. The vibration signal that is thus reflected is received again by the piezo transducer. A position of the point of contact on the reference element is determined from a time difference between transmission and reception. The position of the component in relation to the piezo transducer may thus be determined in a simple and reliable manner, and abrasion due to direct contact between the piezo transducer and the component may be avoided.

In one embodiment, the vibration signal is generated on an edge of the reference element. The edge is in touching contact with the component. The edge offers an advantageous propagation path for the vibration signal. The vibration signal travels along the edge in the form of a transverse wave that may be reflected particularly well and may therefore be received with a good signal-noise ratio.

The point of contact between the moveable component and the reference element may be generated by attaching a sliding or rolling element of the moveable component onto the edge of the reference element. This reduces the friction between the leaf and the reference element, such that abrasion is essentially avoided. To attach the sliding or rolling element (e.g., using magnetic forces), the sliding or rolling element and the reference element are magnetized. This dispenses with the need for mechanical elements to attach the two elements to each other such that abrasion is avoided.

In one embodiment, a contact pressure of 5 to 10 N may be used in order to allow a good reflection of the vibration signal that has been received.

BRIEF DESCRIPTION OF THE DRAWINGS

FIG. 1 shows a leaf of a multi-leaf collimator with one embodiment of a device.

DETAILED DESCRIPTION OF THE DRAWINGS

The mode of operation of one embodiment of a device for the determination of a position of a component that is moveable in a linear manner along at least one axis is explained below with reference to the embodiment of a multi-leaf collimator.

A multi-leaf collimator for therapeutic irradiation of tumors, for example, includes a plurality of leaves 10 that are moveable in a path of an X-ray beam. Through the movement of the leaves 10, which is provided by a mechanism that is not shown in the figure, a cross-sectional profile of the beam path may be shaped, and an adjustment may be made to match the contour of the perimeter of a tissue segment that is to be irradiated. In modern radio-therapeutic methods, the leaf position is adjusted dynamically in order, for example, to modulate the intensity of the radiation or, where there is a relative movement between the beam and the patient, to adjust a cross-sectional profile of the beam to match the perimeter contour that is a function of a respective angular position between the patient and the beam.

In order to achieve a reliable irradiation level (e.g., to concentrate the maximum desired radiation intensity onto the tissue that is to be irradiated while the surrounding tissue is irradiated as little as possible and is therefore damaged as little as possible), the position of the leaf 10 is known precisely at all times. To achieve this, the multi-leaf collimator has a panel 12 that extends in a direction of the movement of the leaf 10 (e.g., in the direction of the arrow 14). A support 16, in which a rolling bearing 18 is arranged, is mounted on the leaf 10. The rolling bearing 18 runs along an edge 20 of the panel 12.

To determine the position of the leaf 10, a piezo transducer 22 is arranged on the edge 20 of the panel 12. In order to measure the position of the leaf 10, a vibration is initiated by the piezo transducer 22 in the panel 12. This vibration is reflected as a transverse edge wave in a direction of the arrow 24 along the edge 20 and is reflected on the support point for the roller 18. The reflected wave travels back to the piezo transducer 22 and is received by the piezo transducer 22, travelling in an opposite direction to the original edge wave. From the propagation time of the original wave and of the reflected wave, the distance between the piezo transducer 22 and the support point for the roller 18 may be determined. The current position of the leaf 10 may be calculated from the determined distance between the piezo transducer 22 and the support point for the roller 18.

In order to allow a reliable detection of the reflected wave (e.g., to achieve a high signal-noise ratio), the contact pressure of the roller 18 onto the edge 20 of the panel 12 may be around 5 to 10 N. In order to achieve such a contact pressure with a minimum mechanical outlay and minimum abrasion, the roller 18 and the panel 12 may be magnetized. For example, there is an option for using ferromagnetic (e.g., permanently magnetic) materials. The magnetization of the roller 18 may be arranged to be parallel to the axis 26 thereof.

In order to achieve both a well-defined support point for the roller 18 and minimum abrasion between the roller 18 and the edge 20 during movement of the leaf 10, the roller 18 may run in a groove arranged in the edge 20. In order to achieve the aforementioned objectives, the roller 18 rests on the bottom of the groove and does not, however, touch side walls of the groove. A conical design of the groove may be used. In order to avoid unwanted forces between the roller 18 and the side walls of the groove, side surfaces of the roller 18 and the side walls of the groove are coated with non-magnetic materials, such that the force between the magnetized roller 18 and the magnetized panel 12 is advantageously directed onto the bottom of the groove.

A multi-leaf collimator with low abrasion is created, since the piezo transducer, for example, is not in moveable contact with other components. This also leads to an improved transmission of vibrations, the result of which is a higher amplitude for the surface wave that travels along the edge 20. This again results in a more intensively reflected wave that, as a result of the improved transmission of vibrations to the piezo transducer 22, leads to a clear increase in the echo amplitude and hence to an improved signal-noise ratio. In addition, the use of magnetic rollers 18 on magnetic panels 12 leads to less force being exerted in the roller bearings and thus to reduced abrasion in the roller bearing, as a result of dispensing with the need for other mechanical power-generating systems such as springs, for example.

The invention is of course not limited to the embodiment of a multi-leaf collimator that is described here by way of example. On the same basis, the position of any other components that are moveable in a linear manner may be determined. Examples of this are examination couches for medical devices, measurement equipment, optical instruments, machine tools or any other components.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for determining a position of a component that is moveable in a linear manner along an assigned axis, the device comprising:
    a reference element that extends in a direction of the assigned axis, the reference element being assigned to the component, the component operable to be brought into mechanical contact with the reference element; and
    a piezo transducer arranged on the reference element, the piezo transducer operable to generate and receive vibrations in the material used for the reference element,
    wherein the component is in mechanical contact with an edge of the reference element, on which the piezo transducer is arranged,
    wherein the mechanical contact between the component and the reference element is created with a sliding or rolling element, and
    wherein the sliding or rolling element is moveable in a groove of the reference element.

2. The device as claimed in claim 1, wherein the reference element comprises a panel that is attached to a supporting frame.

3. The device as claimed in claim 1, wherein there is a contact pressure of 5-10 N. between the sliding or rolling element and the reference element.

4. The device as claimed in claim 1, wherein the reference element and the sliding or rolling element are magnetized.

5. The device as claimed in claim 1, wherein the groove is conically shaped.

6. The device as claimed in claim 1, wherein side walls of the groove are coated with a non-magnetic material.

7. The device as claimed in claim 1, wherein side surfaces of the sliding or rolling element are coated with a non-magnetic material.

8. The device as claimed in claim 1, wherein the device is configured to determine a position of a leaf of a multi-leaf collimator operable to shape a beam in an X-ray device.

9. The device as claimed in claim 1, wherein the device is configured to determine a position of an examination couch of a medical device.

10. A method for determining a position of a component that is moveable in a linear manner along at least one assigned axis, the method comprising:
    generating a vibration signal in a reference element using a piezo transducer that is affixed to the reference element, the reference element extending in a direction of the at least one assigned axis; and
    receiving a vibration signal that is reflected on a point of contact between the component and the reference element, a position of the point of contact on the reference element being determined from a time difference between generation and the reception.

11. The method as claimed in claim 10, wherein generating the vibration signal comprises generating the vibration signal on an edge of the reference element, the edge being in touching contact with the component.

12. The method as claimed in claim 11, further comprising generating the point of contact between the component and the reference element by attaching a sliding or rolling element of the component to the edge of the reference element.

13. The method as claimed in claim 12, wherein the sliding or rolling element is attached magnetically.

14. The method as claimed in claim 12, wherein the sliding or rolling element is attached with a force of 5-10 N.

15. The method as claimed in claim 10, further comprising generating the point of contact between the component and the reference element by attaching a sliding or rolling element of the component to an edge of the reference element.

16. The method as claimed in claim 15, wherein the sliding or rolling element is attached magnetically.

17. The method as claimed in claim 13, wherein the sliding or rolling element is attached with a force of 5-10 N.

18. A device for determining a position of a component that is moveable in a linear manner along an assigned axis, the device comprising:
    a reference element that extends in a direction of the assigned axis, the reference element being assigned to the component, the component operable to be brought into mechanical contact with the reference element; and
    a piezo transducer arranged on the reference element, the piezo transducer operable to generate and receive vibrations in the material used for the reference element,
    wherein the component is in mechanical contact with an edge of the reference element, on which the piezo transducer is arranged,
    wherein the mechanical contact between the component and the reference element is created with a sliding or rolling element, and
    wherein the reference element and the sliding or rolling element are magnetized.

* * * * *